(12) United States Patent
Baker, Jr.

(10) Patent No.: US 8,007,441 B2
(45) Date of Patent: *Aug. 30, 2011

(54) PULSE OXIMETER WITH ALTERNATE HEART-RATE DETERMINATION

(75) Inventor: Clark R. Baker, Jr., Newman, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 44 days.

This patent is subject to a terminal disclaimer.

(21) Appl. No.: 12/437,335

(22) Filed: May 7, 2009

(65) Prior Publication Data

US 2009/0221889 A1  Sep. 3, 2009

Related U.S. Application Data

(63) Continuation of application No. 10/796,566, filed on Mar. 8, 2004, now Pat. No. 7,534,212.

(51) Int. Cl.
*A61B 5/02* (2006.01)
(52) U.S. Cl. ........................ 600/500; 600/324
(58) Field of Classification Search .......... 600/323–341, 600/500–507
See application file for complete search history.

(56) References Cited

U.S. PATENT DOCUMENTS

| | | | |
|---|---|---|---|
| 3,638,640 A | 2/1972 | Shaw | |
| 4,714,341 A | 12/1987 | Hamaguri et al. | |
| 4,805,623 A | 2/1989 | Jöbsis | |
| 4,807,631 A | 2/1989 | Hersh et al. | |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |

(Continued)

FOREIGN PATENT DOCUMENTS

EP    1006863    10/2003

(Continued)

OTHER PUBLICATIONS

Leahy, Martin J., et al.; "Sensor Validation in Biomedical Applications," *IFAC Modelling and Control in Biomedical Systems,* Warwick, UK; pp. 221-226 (1997).

Barreto, Armando B., et al.; "Adaptive LMS Delay Measurement in dual Blood Volume Pulse Signals for Non-Invasive Monitoring," *IEEE,* pp. 117-120 (1997).

East, Christine E., et al.; "Fetal Oxygen Saturation and Uterine Contractions During Labor," *American Journal of Perinatology,* vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society,* vol. 20, No. 6, p. 3072-3075, 1998.

(Continued)

*Primary Examiner* — Charles A Marmor, II
*Assistant Examiner* — Karen E Toth

(57) ABSTRACT

A pulse oximeter which determines multiple heart rates, and selects between them based on the metrics of only one of the heart rate calculations. A primary heart rate calculation method is selected, and is used unless its metrics indicate questionable accuracy, in which case an alternative rate calculation is available and is used instead.

19 Claims, 3 Drawing Sheets

U.S. PATENT DOCUMENTS

| | | | |
|---|---|---|---|
| 5,279,295 A | 1/1994 | Martens et al. | |
| 5,297,548 A | 3/1994 | Pologe | |
| 5,355,880 A | 10/1994 | Thomas et al. | |
| 5,365,934 A * | 11/1994 | Leon et al. | 600/517 |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,485,847 A | 1/1996 | Baker et al. | |
| 5,524,631 A | 6/1996 | Zahorian et al. | |
| 5,553,614 A | 9/1996 | Chance | |
| 5,558,086 A | 9/1996 | Smith et al. | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,645,059 A | 7/1997 | Fein et al. | |
| 5,645,060 A | 7/1997 | Yorkey | |
| 5,680,857 A | 10/1997 | Pelikan et al. | |
| 5,692,503 A | 12/1997 | Kuenstner | |
| 5,730,124 A | 3/1998 | Yamauchi | |
| 5,758,644 A | 6/1998 | Diab et al. | |
| 5,759,157 A | 6/1998 | Harada et al. | |
| 5,779,631 A | 7/1998 | Chance | |
| 5,782,757 A | 7/1998 | Diab et al. | |
| 5,786,592 A | 7/1998 | Hök | |
| 5,797,840 A | 8/1998 | Akselrod et al. | |
| 5,830,136 A | 11/1998 | Delonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,035,223 A | 3/2000 | Baker, Jr. | |
| 6,064,898 A | 5/2000 | Aldrich | |
| 6,081,742 A | 6/2000 | Amano et al. | |
| 6,083,172 A | 7/2000 | Baker, Jr. et al. | |
| 6,088,607 A | 7/2000 | Diab et al. | |
| 6,120,460 A | 9/2000 | Abreu | |
| 6,134,460 A | 10/2000 | Chance | |
| 6,150,951 A | 11/2000 | Olejniczak | |
| 6,154,667 A | 11/2000 | Miura et al. | |
| 6,157,850 A | 12/2000 | Diab et al. | |
| 6,163,715 A | 12/2000 | Larsen et al. | |
| 6,178,343 B1 | 1/2001 | Bindszus et al. | |
| 6,181,958 B1 | 1/2001 | Steuer et al. | |
| 6,181,959 B1 | 1/2001 | Schollermann et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,374,129 B1 | 4/2002 | Chin et al. | |
| 6,397,091 B2 | 5/2002 | Diab et al. | |
| 6,408,198 B1 | 6/2002 | Hanna et al. | |
| 6,411,833 B1 | 6/2002 | Baker et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,449,501 B1 | 9/2002 | Reuss | |
| 6,461,305 B1 | 10/2002 | Schnall | |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,580,086 B1 | 6/2003 | Schulz et al. | |
| 6,584,336 B1 | 6/2003 | Ali et al. | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Pishney et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,836,679 B2 | 12/2004 | Baker, Jr. et al. | |
| 6,850,053 B2 | 2/2005 | Daalmans et al. | |
| 6,852,083 B2 | 2/2005 | Caro et al. | |
| 6,862,091 B2 | 3/2005 | Johnson | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,939,307 B1 | 9/2005 | Dunlop | |
| 6,944,488 B2 | 9/2005 | Roberts et al. | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,006,856 B2 | 2/2006 | Baker, Jr. et al. | |
| 7,016,715 B2 | 3/2006 | Stetson | |
| 7,024,235 B2 | 4/2006 | Melker et al. | |
| 7,025,730 B2 | 4/2006 | Cho et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,056 B2 | 5/2006 | Hannula et al. | |
| 7,083,593 B2 | 8/2006 | Stultz | |
| 7,085,597 B2 | 8/2006 | Fein et al. | |
| 7,127,278 B2 | 10/2006 | Melker et al. | |
| 7,130,671 B2 | 10/2006 | Baker, Jr. et al. | |
| 7,162,306 B2 | 1/2007 | Caby et al. | |
| 7,209,775 B2 | 4/2007 | Bae et al. | |
| 7,236,811 B2 | 6/2007 | Schmitt | |
| 7,263,395 B2 | 8/2007 | Chan et al. | |
| 7,272,426 B2 | 9/2007 | Schmid | |
| 7,302,284 B2 | 11/2007 | Baker, Jr. et al. | |
| 7,315,753 B2 | 1/2008 | Baker, Jr. et al. | |
| 7,336,983 B2 | 2/2008 | Baker, Jr. et al. | |
| 7,373,193 B2 | 5/2008 | Al-Ali et al. | |
| 7,379,769 B2 | 5/2008 | Piron et al. | |
| 7,398,115 B2 | 7/2008 | Lynn | |
| 7,400,918 B2 | 7/2008 | Parker et al. | |
| 7,455,643 B1 | 11/2008 | Li et al. | |
| 7,499,740 B2 * | 3/2009 | Nordstrom et al. | 600/323 |
| 7,534,212 B2 * | 5/2009 | Baker, Jr. | 600/500 |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |

| | | |
|---|---|---|
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0072660 A1 | 6/2002 | Diab et al. |
| 2002/0111748 A1 | 8/2002 | Kobayashi et al. |
| 2002/0128544 A1* | 9/2002 | Diab et al. .................... 600/323 |
| 2002/0133068 A1 | 9/2002 | Huiku |
| 2002/0137994 A1 | 9/2002 | Baker et al. |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0109798 A1* | 6/2003 | Kermani ....................... 600/547 |
| 2003/0139687 A1 | 7/2003 | Abreu |
| 2003/0144584 A1 | 7/2003 | Mendelson |
| 2003/0163057 A1 | 8/2003 | Flick et al. |
| 2003/0220548 A1 | 11/2003 | Schmitt |
| 2003/0220576 A1 | 11/2003 | Diab |
| 2004/0010188 A1 | 1/2004 | Wasserman |
| 2004/0015091 A1 | 1/2004 | Greenwald et al. |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0138540 A1 | 7/2004 | Baker et al. |
| 2004/0158135 A1 | 8/2004 | Baker, Jr. et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0181134 A1 | 9/2004 | Baker et al. |
| 2004/0230106 A1 | 11/2004 | Schmitt et al. |
| 2005/0043599 A1 | 2/2005 | O'Mara |
| 2005/0080323 A1 | 4/2005 | Kato |
| 2005/0085735 A1 | 4/2005 | Baker, Jr. et al. |
| 2005/0101850 A1 | 5/2005 | Parker |
| 2005/0113651 A1 | 5/2005 | Wood et al. |
| 2005/0113656 A1 | 5/2005 | Chance |
| 2005/0119543 A1 | 6/2005 | Parker et al. |
| 2005/0119586 A1 | 6/2005 | Coyle et al. |
| 2005/0143634 A1 | 6/2005 | Baker, Jr. |
| 2005/0154370 A1 | 7/2005 | Sigg et al. |
| 2005/0168722 A1 | 8/2005 | Forstner et al. |
| 2005/0177034 A1 | 8/2005 | Beaumont |
| 2005/0188991 A1 | 9/2005 | Sun et al. |
| 2005/0192488 A1 | 9/2005 | Bryenton et al. |
| 2005/0192500 A1 | 9/2005 | Caro et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0030766 A1 | 2/2006 | Stetson |
| 2006/0052680 A1 | 3/2006 | Diab |
| 2006/0058683 A1 | 3/2006 | Chance |
| 2006/0064024 A1 | 3/2006 | Schnall |
| 2006/0122475 A1 | 6/2006 | Balberg et al. |
| 2006/0135860 A1 | 6/2006 | Baker, Jr. et al. |
| 2006/0195028 A1 | 8/2006 | Hannula et al. |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0217774 A1 | 9/2006 | Mower et al. |
| 2006/0224058 A1 | 10/2006 | Mannheimer |
| 2006/0229510 A1 | 10/2006 | Fein et al. |
| 2006/0229511 A1 | 10/2006 | Fein et al. |
| 2006/0241975 A1 | 10/2006 | Brown |
| 2006/0247501 A1 | 11/2006 | Ali |
| 2006/0247506 A1 | 11/2006 | Balberg et al. |
| 2006/0258921 A1 | 11/2006 | Addison et al. |
| 2006/0285736 A1 | 12/2006 | Brown |
| 2008/0059249 A1 | 3/2008 | Joao |
| 2008/0059250 A1 | 3/2008 | Joao |
| 2008/0132771 A1 | 6/2008 | Parker et al. |

FOREIGN PATENT DOCUMENTS

| | | |
|---|---|---|
| EP | 1006864 | 10/2003 |
| EP | 1491135 | 12/2004 |
| JP | 3170866 | 7/1991 |
| JP | 7124138 | 5/1995 |
| JP | 7136150 | 5/1995 |
| JP | 2003194714 | 7/2003 |
| JP | 2003210438 | 7/2003 |
| JP | 2004008572 | 1/2004 |
| JP | 2004113353 | 4/2004 |
| JP | 2004194908 | 7/2004 |
| JP | 2004248819 | 9/2004 |
| JP | 2004290545 | 10/2004 |
| WO | WO 9101678 | 2/1991 |
| WO | WO 9309711 | 5/1993 |
| WO | WO 9608992 | 3/1996 |
| WO | WO 9843071 | 10/1998 |
| WO | WO 9932030 | 7/1999 |
| WO | WO 0021438 | 4/2000 |
| WO | WO 03084396 | 10/2003 |
| WO | WO 2004075746 | 9/2004 |
| WO | WO 2005025399 | 3/2005 |

OTHER PUBLICATIONS

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Kaestle, S.; "Determining Artefact Sensitivity of New Pulse Oximeters in Laboratory Using Signals Obtained from Patient," *Biomedizinische Technik*, vol. 45 (2000).

Belal, Suliman Yousef, et al.; "A fuzzy system for detecting distorted plethysmogram pulses in neonates and paediatric patients," *Physiol. Meas.*, vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

J. Huang, et al.; "Low Power Motion Tolerant Pulse Oximetry," *Abstracts*, A7, p. S103. (undated).

Hamilton, Patrick S., et al.; "Effect of Adaptive Motion-Artifact Reduction on QRS Detection," *Biomedical Instrumentation & Technology*, pp. 197-202 (undated).

Odagiri, Y.; "Pulse Wave Measuring Device," *Micromechatronics*, vol. 42, No. 3, pp. 6-11 (undated) (Article in Japanese—contains English summary of article).

Cysewska-Sobusaik, Anna; "Metrological Problems With noninvasive Transillumination of Living Tissues," *Proceedings of SPIE*, vol. 4515, pp. 15-24 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

* cited by examiner

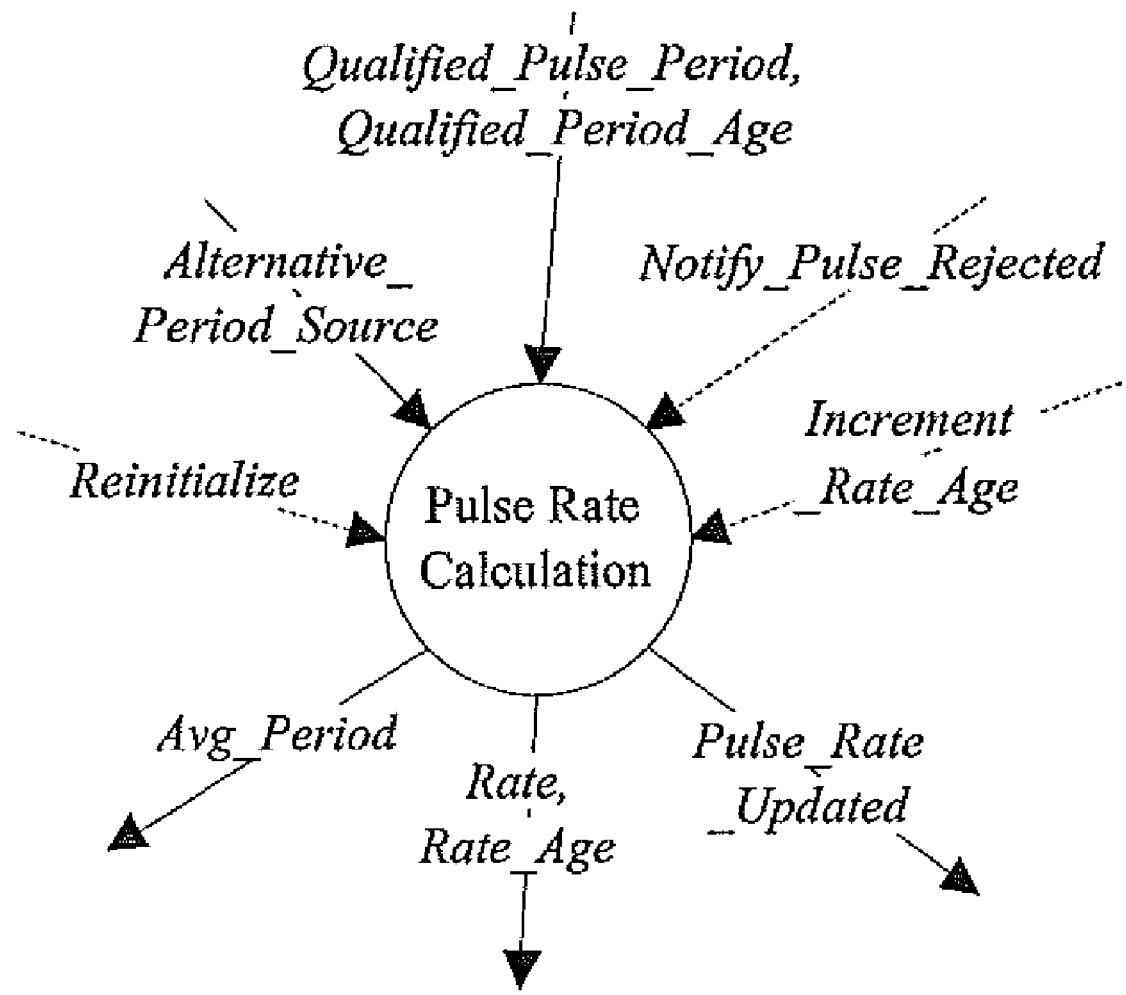
FIG. 3 Context Diagram for
Pulse Rate Calculation Subsystem

US 8,007,441 B2

PULSE OXIMETER WITH ALTERNATE HEART-RATE DETERMINATION

CROSS-REFERENCES TO RELATED APPLICATIONS

This application is a continuation of U.S. patent application Ser. No. 10/796,566, filed Mar. 8, 2004, the disclosure of which is hereby incorporated by reference in its entirety for all purposes.

BACKGROUND OF THE INVENTION

The present invention relates to oximeters, and in particular to determining a pulse rate by multiple mechanisms in a detected waveform from a pulse oximeter.

Pulse oximetry is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed at various wavelengths is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

U.S. Pat. No. 6,083,172, No. 5,853,364 and No. 6,411,833 show multiple methods of calculating a pulse rate in a pulse oximeter, with a "best rate" module which arbitrates between the pulse rate calculations to select a best rate based on confidence levels associated with each. The confidence levels are calculated using various metrics to determine the reliability of the different pulse rate calculations. Also, U.S. Pat. No. 5,524,631 shows a fetal heart rate monitor that uses multiple parallel filter paths to identify the fetal heart rate, and uses a figure of merit operation to weight the different heart rate estimates.

N-100. The N-100 technology, dating to around 1985, accepted or rejected pulses based on pulse history of the size of pulses, pulse shape, expected time to occur (frequency) and ratio of R/IR.

In particular, the N-100 found pulses by looking for a signal maximum, followed by a point of maximum negative slope, then a minimum. The processing was done in a state machine referred to as "munch." Each maximum was not qualified until the signal passed below a noise threshold, referred to as a noise gate. This acted as an adaptive filter since the noise gate level was set by feedback from a subsequent processing step to adapt to different expected signal amplitudes. The pulses are then accepted or rejected in a "Level3" process which was a filter which adapts to changing signals by comparing the amplitude, period and ratio-of-ratios (ratio of Red to IR, with Red and IR being expressed as a ratio of AC to DC) of a new pulse to the mean of values in a history buffer, then determining if the difference is within a confidence level. If the new pulse was accepted, the history buffer was updated with the values for the new pulse. The level3 process acted as an adaptive bandpass filter with center-frequency and bandwidth (confidence limits) being adapted by feedback from the output of the filter.

N-200. The N-200 improved on the N-100 since it could be synchronized with an ECG, and included ECG filtering. The N-200 also added interpolation to compensate for baseline shift between the time of measuring the pulse maximum and minimum. The N-200 included other filtering features as well, such as a "boxcar" filter which computed the mean of a varying number of signal samples.

The N-200, after various filtering and scaling steps, applies the digitized signals to a "boxcar" filter, which computes the mean of N samples, where N is set by feedback from a subsequent processing step according to the filtered heart rate. New samples are averaged into the boxcar filter, while the oldest samples are dropped. The boxcar length (N) is used to set three parameters: a pulse threshold, absolute minimum pulse and small pulse. An ensemble-averaging (a.k.a "slider") filter then produces a weighted average of the new samples and the previous ensemble-averaged sample from one pulse-period earlier. The samples are then passed to a "munch" state machine and a noise gate, like the N-100. An interpolation feature is added to the N-100 process, to compensate for changes in the baseline level. Since the minimum and maximum occur at different times, a changing baseline may increase or decrease the minimum and not the maximum, or vice-versa.

"Ensemble averaging" is an integral part of C-Lock, which is NELLCOR's trademark for the process of averaging samples from multiple pulses together to form a composite pulse. This process is also known as "cardiac-gated averaging." It requires a "trigger" event to mark the start of each pulse.

BRIEF SUMMARY OF THE INVENTION

The present invention is a pulse oximeter which determines multiple heart rates, and selects between them based on the metrics of only one of the heart rate calculations. A primary heart rate calculation method is selected, and is used unless its metrics indicate questionable accuracy, in which case an alternative rate calculation is available and is used instead.

In one embodiment, the primary heart rate calculation method does not use an ensemble averaged waveform, while the alternative heart rate calculation does use an ensemble averaged waveform. The alternative heart rate calculation is used if the primary calculation has disqualified its most recently detected pulse.

BRIEF DESCRIPTION OF THE DRAWINGS

FIG. 3 is a context diagram of the pulse rate calculation subsystem.

DETAILED DESCRIPTION OF THE INVENTION

Figure 1:
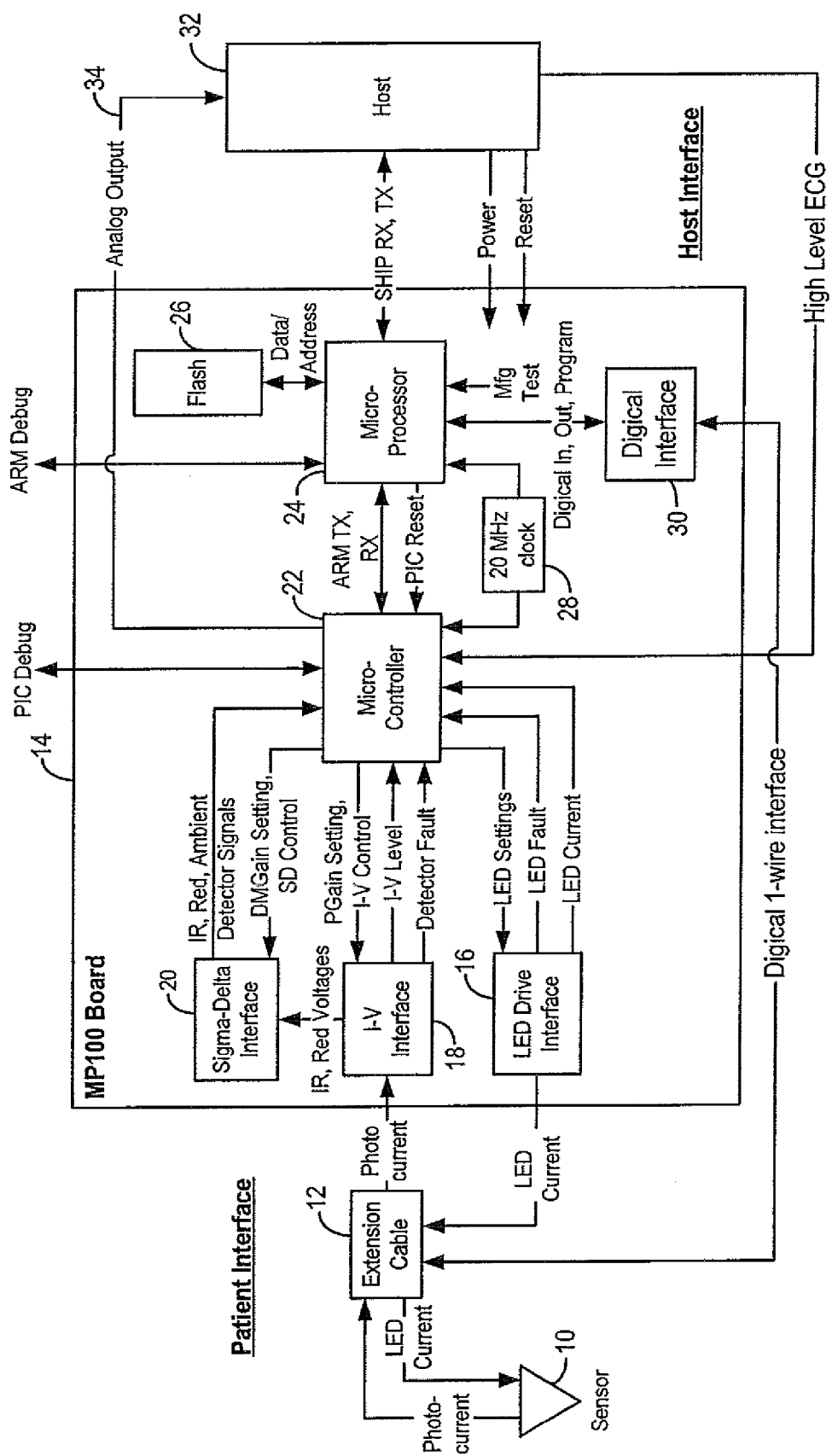
FIG. 1 is a block diagram of an oximetry system incorporating an embodiment of the invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22 which includes a 10-bit A/D converter. Controller 22 includes flash memory for a program, and EEPROM memory for data. The processor also includes a controller chip 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

Design Summary The design of the present invention is intended to deal with unwanted noise. Signal metrics are measured and used to determine filter weighting. Signal metrics are things that indicate if a pulse is likely a plethysmograph or noise, such as frequency (is it in the range of a human heart rate), shape (is it shaped like a heart pulse), rise time, etc. A similar technique was used in the Nellcor N200, described in the background of this application. The new design adds a number of different features and variations, such as the use of two ensemble averagers as claimed in the present invention.

Figure 2:
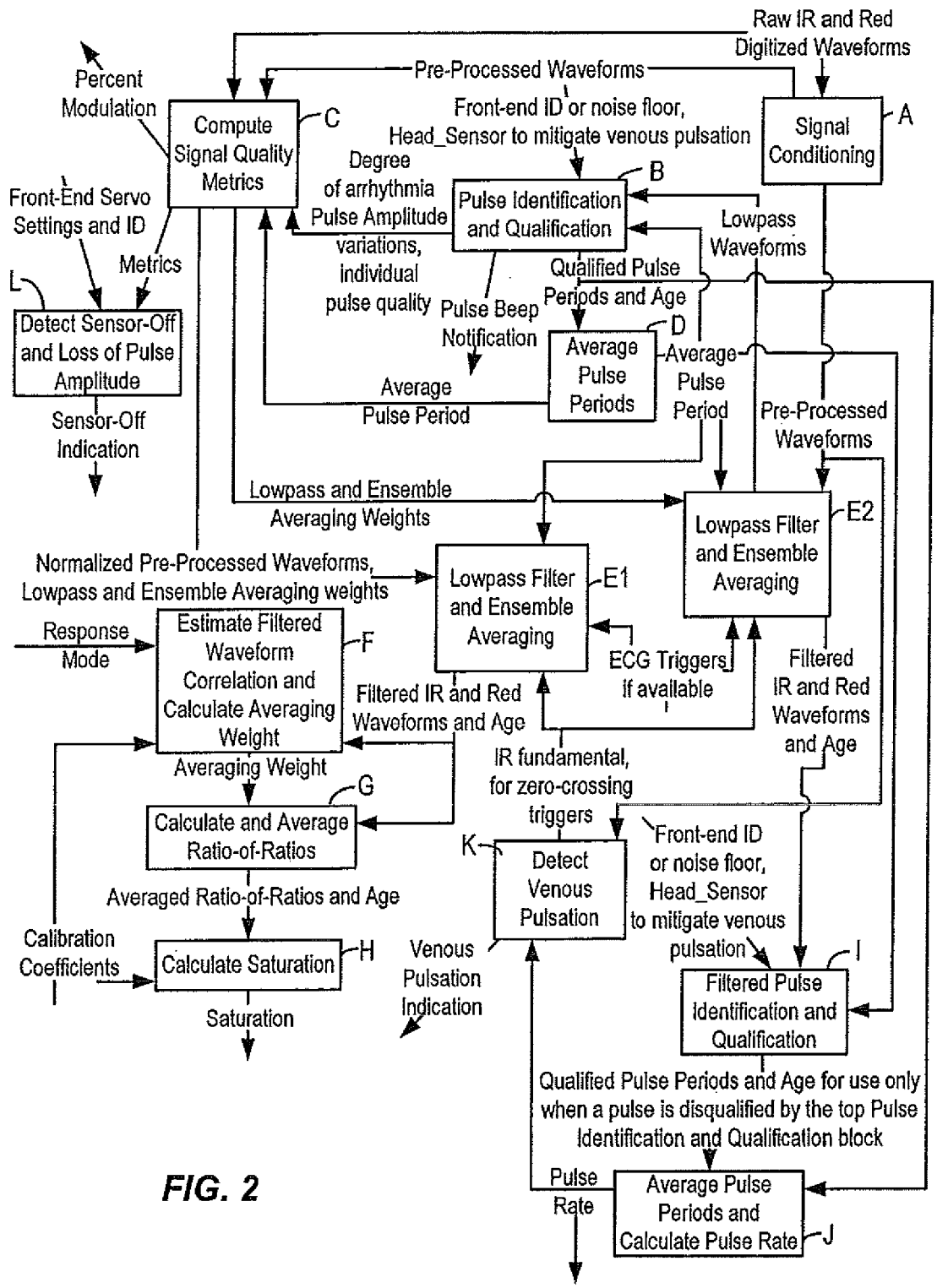
FIG. 2 is a diagram of the software processing blocks of an oximeter including an embodiment of the present invention.

Details of the architecture are shown in the diagram of FIG. 2. This design calculates both the oxygen saturation, and the pulse rate, which are described separately below.

I. Oxygen Saturation Calculation.

Signal Conditioning—The digitized red and IR signals are received and are conditioned in this block by (1) taking the 1st derivative to get rid of baseline shift, (2) low pass filtering with fixed coefficients, and (3) dividing by a DC value to preserve the ratio. The function of the Signal Conditioning subsystem is to emphasize the higher frequencies that occur in the human plethysmograph and to attenuate low frequencies in which motion artifact is usually concentrated. The Signal Conditioning subsystem selects its filter coefficients (wide or narrow band) based on hardware characteristics identified during initialization.

Inputs—digitized red and IR signals

Outputs—Pre-processed red and IR signals

Pulse Identification and Qualification—The low pass filtered and digitized red and IR signals are provided to this block to identify pulses, and qualify them as likely arterial pulses. This is done using a pre-trained neural net, and is primarily done on the JR signal. The pulse is identified by examining its amplitude, shape and frequency, just as was done in the Nellcor N-100. An input to this block is the average pulse period from block D. This function is similar to the N-100, which changed the upfront qualification using the pulse rate. The output indicates the degree of arrhythmia and individual pulse quality.

Inputs—(1) Pre-processed red and IR signals, (2) Ave. pulse period, (3) Lowpass Waveforms from the low pass filter.

Outputs—(1) Degree of arrhythmia, (2) pulse amplitude variations, (3) individual pulse quality, (4) Pulse beep notification, (5) qualified pulse periods and age.

C. Compute Signal Quality Metrics—This block determines the pulse shape (derivative skew), period variability, pulse amplitude and variability, Ratio of Ratios variability, and frequency content relative to pulse rate.

Inputs—(1) raw digitized red and IR signals, (2) degree of arrhythmia, individual pulse quality, pulse amplitude variation (3) pre-processed red and IR signals, (4) average pulse period.

Outputs—(1) Lowpass and ensemble averaging filter weights, (2) metrics for sensor off detector, (3) Normalized Pre-processed waveforms, (4) percent modulation.

Average Pulse Periods, This block calculates the average pulse period from the pulses received.

Inputs—Qualified pulse periods and age.

Outputs—Average pulse period.

E1. Lowpass Filter and Ensemble Averaging—Block E1 low pass filters and ensemble averages the signal conditioned by block A, and normalized by block C, for the pulse rate identification. The weights for the low pass filter are determined by the Signal Metrics block C. The signal is also ensemble averaged (this attenuates frequencies other than those of interest near the pulse rate and its harmonics), with the ensemble averaging filter weights also determined by Signal Metrics block C. Less weight is assigned if the signal is flagged as degraded. More weight is assigned if the signal is flagged as arrhythmic because ensemble-averaging is not appropriate during arrhythmia Red and R are processed separately, but with the same filtering weights. The filtering is delayed approximately one second to allow the signal metrics to be calculated first.

The filters use continuously variable weights. If samples are not to be ensemble-averaged, then the weighting for the previous filtered samples is set to zero in the weighted average, and the new samples are still processed through the code. This block tracks the age of the signal—the accumulated amount of filtering (sum of response times and delays in processing). Too old a result will be flagged (if good pulses haven't been detected for awhile).

Inputs—(1) normalized pre-processed red and IR signals, (2) average pulse period, (3) low pass filter weights and ensemble averaging filter weights, (4) ECG triggers, if available, (5) IR fundamental, for zero-crossing triggers.

Outputs—(1) filtered red and IR signals, (2) age.

Estimate Filtered Waveform Correlation and Calculate Averaging Weight—this uses a noise metric similar to that used in the N100 and N200 described above, and doesn't use feedback. The variable weighting for the filter is controlled by the ratio-of-ratios variance. The effect of this variable-weight filtering is that the ratio-of-ratios changes slowly as artifact increases and changes quickly as artifact decreases. The subsystem has two response modes. Filtering in the Fast Mode targets an age metric of 3 seconds. The target age is 5 seconds in Normal Mode. In Fast Mode, the minimum weighting of the current value is clipped at a higher level. In other words, a low weight is assigned to the newest ratio-of-ratios calculation if there is noise present, and a high weight if no noise is present.

Inputs—(1) filtered red and IR signals and age, (2) calibration coefficients, (3) response mode (user speed settings).

Outputs—averaging weight for ratio-of-ratios calculation.

Calculate Saturation—Saturation is calculated using an algorithm with the calibration coefficients and averaged ratio of ratios.

Inputs—(1) Averaged Ratio-of-Ratios, (2) calibration coefficients.

Outputs—Saturation.

II. Pulse Rate Calculation.

E2. Lowpass Filter and Ensemble Averaging—Block E2 low pass filters and ensemble averages the signal conditioned by block A, for the pulse rate identification. The weights for the low pass filter are determined by the Signal Metrics block C. The signal is also ensemble averaged (this attenuates frequencies other than those of interest near the pulse rate and its harmonics), with the ensemble averaging filter weights also determined by Signal Metrics block C. Less weight is assigned if the signal is flagged as degraded. More weight is assigned if the signal is flagged as arrhythmic since filtering is not appropriate during arrhythmia. Red and IR are processed separately. The process of this block is delayed approximately one second to allow the signal metrics to be calculated first.

The filters use continuously variable weights. If samples are not to be ensemble-averaged, then the weighting for the previous filtered samples is set to zero in the weighted average, and the new samples are still processed through the code. This block tracks the age of the signal—the accumulated amount of filtering (sum of response times and delays in processing). Too old a result will be flagged (if good pulses haven't been detected for awhile).

Inputs—(1) pre-processed red and IR signals, (2) average pulse period, (3) Lowpass filter weights and ensemble averaging filter weights, (4) ECG triggers, if available, (5) IR fundamental, for zero-crossing triggers.

Outputs—(1) filtered red and IR signals, (2) age.

Filtered Pulse Identification and Qualification—This block identifies and qualifies pulse periods from the filtered waveforms, and its results are used only when a pulse is disqualified by block B.

Inputs—(1) filtered red and IR signals and age, (2) average pulse period, (3) hardware ID or noise floor, (4) kind of sensor, Outputs—qualified pulse periods and age.

Average Pulse Periods and Calculate Pulse Rate—This block calculates the pulse rate and average pulse period.

Inputs—Qualified pulse periods and age

Outputs—(1) average pulse period, (2) pulse rate.

Venous Pulsation

Detect Venous Pulsation—Block K receives as inputs the pre-processed red and IR signal and age from Block A, and pulse rate and provides an indication of venous pulsation as an output. This subsystem produces an IR fundamental waveform in the time domain using a single-tooth comb filter which is output to the Ensemble Averaging filters.

Inputs—(1) filtered red and IR signals and age, (2) pulse rate.

Outputs—Venous Pulsation Indication, IR fundamental

IV. Sensor Off

Detect Sensor-Off and Loss of Pulse Amplitude—The Pulse Lost and Sensor Off Detection subsystem uses a pre-trained neural net to determine whether the sensor is off the patient. The inputs to the neural net are metrics that quantify several aspects of the behavior of the IR and Red values over the last several seconds. Samples are ignored by many of the oximetry algorithm's subsystems while the Signal State is not either Pulse Present or Sensor Maybe Off. The values of the Signal State variable are: "Pulse Present, Disconnect, Pulse Lost, Sensor Maybe Off, and Sensor Off."

Inputs—(1) metrics, (2) front-end servo settings and ID

Outputs—Signal state including sensor-off indication

Pulse Rate Calculation subsystem

The subsystem averages qualified pulse periods from the Pulse Identification and Qualification subsystem. It outputs the average period and the corresponding pulse rate.

The oximetry algorithm contains two instances of this subsystem. The first instance receives input from the Pulse Identification and Qualification instance whose input waveform have been processed by the Signal Conditioning subsystem, then lowpass filtered, but not ensemble averaged, by the Ensemble Averaging subsystem. The second instance of the Pulse Rate Calculation subsystem receives input from two instances of the Pulse Identification and Qualification subsystem, the one described above and a second instance that receives input that has been ensemble averaged.

Selection of Pulse Period Source

One instance of the subsystem receives qualified pulse periods from two sources. The subsystem selects which of these two sources to use for its pulse rate calculation based solely on analysis of only one source, the "primary" source. The oximetry algorithm designates the Pulse Identification and Qualification instance that does NOT receive ensemble-averaged waveforms as the primary source, and designates the other Pulse Identification and Qualification instance as the "alternate" source of qualified pulse periods. Qualified pulse periods from the alternate source are only used if the most recent pulse from the primary source was rejected. When a qualified pulse period is received from the primary source, it is always used to update the pulse-rate calculation, and will prevent qualified pulse periods from the alternate source from being used until the primary source once again rejects a pulse period, Calculation of Average Pulse Period and Pulse-Rate Estimate When the subsystem uses a Qualified_Pulse_Period, it updates its average pulse period, Avg_Period, using a pulse-based, variable-weight IIR filter, then computes its Rate output from Avg_Period. The steps for this filtering operation are:

1. $r_t = (60/\Delta t)/\text{Qualified\_Pulse\_Period}$
2. $k = \text{Consecutive\_Qualified}/\max(|r_t - r_{t-1}|, |r_{t-1} - r_{t-2}|, |r_{t-2} - r_{t-3}|, 1.0)$
3. $x = \text{bound}(\min(\text{Avg\_Period}_{t-1}, \text{Qualified\_Pulse\_Period}, \frac{3}{4} \text{ seconds}, 2 \text{ seconds})/7 \text{ seconds}$
4. If Rate_Age>10 seconds, $x = \min(x \cdot \text{Rate\_Age}/10 \text{ seconds}, 0.3)$
5. $k = \max(1/\text{Total\_Qualified}, \min(k, x))$
6. If $\text{Avg\_Period}_{t-1} \neq 0$ $\text{Avg\_Period}_t = \text{Avg\_Period}_{t-1} \cdot (\text{Qualified\_Pulse\_Period}/\text{Avg\_Period}_{t-1})^k$
7. If $\text{Avg\_Period}_{t-1} = 0$ $\text{Avg\_Period}_t = \text{Qualified\_Pulse\_Period}$
8. $\text{Rate} = (60/\Delta t)/\text{Avg\_Period}_t$
9. $\text{Rate\_Age} = \text{Rate\_Age} + k \cdot (\text{Qualified\_Period\_Age} - \text{Rate\_Age})$ where:

$r_t$ is the pulse rate corresponding to Qualified_Pulse_Period, in BPM the $_{t-1}$ subscript denotes the previous qualified pulse.

$\Delta t$ is the oximetry algorithm's sample interval in seconds $60/\Delta t$ is the number of samples per minute x is a filter weight that targets a 7-second response time for typical adult pulse rates.

k is the final filter weight, based on both x and the differences between consecutive values of $r_t$. During the first few pulses, k is increased to at least 1/Total_Qualified so that the initial qualified pulses will be weighted equally.

Consecutive_Qualified is the number of consecutive qualified pulses, and Total_Qualified is the total number of pulses qualified since the subsystem was reinitialized. Both Consecutive_Qualified and Total_Qualified are incremented each time a Qualified_Pulse_Period is used, before k is calculated. Consecutive_Qualified is set to zero when a pulse is rejected by the pulse-period source currently in use.

The update formula for Avg_Period$_t$, in step 6 above, is a geometric average of Avg_Period$_t$ and Qualified_Pulse_Period. Geometric averaging helps to keep the subsystem responsive to large pulses-to-pulse period variations, and large, sustained changes in pulse rate.

Once Rate is initialized to a non-zero value, Rate_Age is incremented every sample, whether or not Rate is updated.

Context Diagram

FIG. 3 is a context diagram of the pulse rate calculation subsystem. The subsystem updates its Avg_Period and Rate outputs from Qualified_Pulse_Periods. It uses Qualified_Pulse_Periods from the Alternative_Period_Source only if it last received a Notify_Pulse_Rejected from the primary source. It updates its Rate_Age output based on Qualified_Period_Age. When Rate is updated, the subsystem sets its Pulse_Rate_Updated flag. The Reinitialize input tells the subsystem to reinitialize itself. Increment_Rate_Age notifies the subsystem to increment its Rate_Age every sample once Rate is initialized.

What is claimed is:

1. A method for determining a heart rate in a pulse oximeter comprising:
   using a processor to determine a first heart rate from a pulse oximetry signal using a first method;
   using the processor to determine a second heart rate from the pulse oximetry signal using a second method;
   using the processor to evaluate a reliability of the first heart rate using metrics applied to the pulse oximetry signal;
   using the processor to select the first heart rate when the metrics indicate the first method is reliable;
   using the processor to select the second heart rate only when the metrics indicate that the first heart rate is unreliable; and
   using the processor to provide an indication on a display of the first heart rate or the second heart rate.

2. The method of claim 1, comprising using the processor to determine that the first heart rate is unreliable when the metrics indicate that a most recent pulse is rejected.

3. The method of claim 1, wherein the first method does not use an ensemble averaged waveform, and the second method does use an ensemble averaged waveform.

4. The method of claim 1, comprising filtering the pulse oximetry signal with a low pass filter.

5. The method of claim 4, wherein filter weights for the low pass filter are determined using the metrics applied to the pulse oximetry signal.

6. The method of claim 5, wherein the metrics comprise one or more of pulse shape, period variability, pulse amplitude and variability, ratio of ratios variability, or frequency content relative to pulse rate.

7. The method of claim 1, wherein using the processor to determine a first or second heart rate comprises determining a pulse period.

8. A pulse oximetry system, comprising:
   a sensor adapted to provide a signal related to a physiological constituent; and
   a monitor adapted to process the signal to determine a pulse period, the monitor comprising:
     software configured to identify one or more qualified pulses from the signal, wherein the one or more qualified pulses comprise likely arterial pulses;
     software configured to determine a first pulse period from the one or more qualified pulses using a first method;
     software adapted to determine a second pulse period from the one or more qualified pulses using a second method;
     an evaluator configured to determine the reliability of the first pulse period using metrics applied to the pulse oximetry signal; and
     a selector configured to use the first pulse period when the metrics indicate the first pulse period is reliable, and to use the second pulse period only when the metrics indicate that the first pulse period is unreliable.

9. The system of claim 8, wherein the first method does not use an ensemble averaged waveform, and the second method does use an ensemble averaged waveform.

10. The system of claim 8, wherein the first pulse period or the second pulse period is converted into a heart rate.

11. The system of claim 8, wherein the first pulse period is unreliable when the metrics indicate that a most recent pulse is rejected.

12. The system of claim 8, comprising software configured to update the pulse period using a pulse-based variable-weight filter.

13. The system of claim 8, wherein the system is configured to filter the signal with a low pass filter.

14. The system of claim 13, wherein filter weights for the low pass filter are determined using the metrics applied to the signal.

15. The system of claim 14 wherein the metrics comprise one or more of pulse shape, period variability, pulse amplitude and variability, ratio of ratios variability, or frequency content relative to pulse rate.

16. The system of claim 8, wherein the software configured to identify one or more qualified pulses from the signal comprises a neural net.

17. The system of claim 8, wherein the software configured to identify one or more qualified pulses from the signal comprises a state machine.

18. A method for determining a heart rate in a pulse oximeter comprising:
   using a processor to determine a first pulse period from a pulse oximetry signal using a first method;
   using the processor to evaluate a reliability of the first pulse period using metrics applied to the pulse oximetry signal;
   using the processor to determine a second pulse period from the pulse oximetry signal using a second method only when the metrics indicate that the first pulse period is unreliable;
   using the processor to convert the first pulse period into a heart rate when the metrics indicate that the first pulse period is reliable;
   using the processor to convert the second pulse period into a heart rate only when the metrics indicate that the first pulse period is unreliable; and
   using the processor to provide an indication on a display of the heart rate.

19. The method of claim 18, wherein the first method does not use an ensemble averaged waveform, and wherein the second method does use an ensemble averaged waveform.

* * * * *